United States Patent
Lo et al.

(10) Patent No.: US 9,538,928 B2
(45) Date of Patent: Jan. 10, 2017

(54) NEURAL RECORDING SYSTEM

(71) Applicant: THE REGENTS OF THE UNIVERSITY OF CALIFORNIA, Oakland, CA (US)

(72) Inventors: Yi-Kai Lo, Los Angeles, CA (US); Wentai Liu, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 159 days.

(21) Appl. No.: 14/108,118

(22) Filed: Dec. 16, 2013

(65) Prior Publication Data
US 2014/0180052 A1 Jun. 26, 2014

Related U.S. Application Data

(63) Continuation of application No. PCT/US2012/043173, filed on Jun. 19, 2012.
(Continued)

(51) Int. Cl.
*A61B 5/04* (2006.01)
*A61B 5/0476* (2006.01)
(Continued)

(52) U.S. Cl.
CPC ....... *A61B 5/04001* (2013.01); *A61B 5/04012* (2013.01); *A61B 5/0476* (2013.01);
(Continued)

(58) Field of Classification Search
CPC .............. H03F 3/45094; H03F 3/45107; H03F 3/45134; H03F 3/45121; H03F 3/45147; H03F 3/45161; H03F 3/45192; H03F 3/45206; H03F 3/45219; H03F 3/45233; H03F 3/45246; H03F 3/4526; H03F 3/45291
See application file for complete search history.

(56) References Cited

U.S. PATENT DOCUMENTS 4,766,394 A * 8/1988 Yukawa ................ H03F 3/3028
330/253
5,831,542 A * 11/1998 Thomas ................ A01C 7/105
310/345
(Continued)

FOREIGN PATENT DOCUMENTS

JP 2003101358 A 4/2003
WO 2012177654 A2 12/2012

OTHER PUBLICATIONS

Thanachayanont et al. "Low-Voltage wideband compact CMOS variable gain amplifier" Electronics Letters vol. 41. No. 2 Jan. 2005.*
(Continued)

*Primary Examiner* — Michael C Stout
(74) *Attorney, Agent, or Firm* — O'Banion & Ritchey LLP; John P. O'Banion

(57) ABSTRACT

A neuron recording system was provided. By using the gain-boosted topology, the amplifier input impedance can be increased while simultaneously reducing the noise. The system can be configured to record local field potentials (LFPs) and neuron spikes, respectively, with low-power consumption. With the flexible digital controller module (DCM), any subset of the recording channels can be activated for recording with independent sampling rate at each channel. A wireless interface to transmit recorded neuron data and an on-chip neuron processor to perform real-time signal processing can be incorporated in the system.

15 Claims, 6 Drawing Sheets

Related U.S. Application Data

(60) Provisional application No. 61/571,098, filed on Jun. 20, 2011.

(51) Int. Cl.
  *H03F 3/45* (2006.01)
  *A61B 5/0478* (2006.01)
  *A61B 5/0482* (2006.01)
  *A61B 5/00* (2006.01)

(52) U.S. Cl.
  CPC ........ *A61B 5/0478* (2013.01); *A61B 5/0482* (2013.01); *A61B 5/7225* (2013.01); *H03F 3/45192* (2013.01); *H03F 3/45475* (2013.01); *H03F 3/45928* (2013.01); *A61B 5/7203* (2013.01); *H03F 2200/165* (2013.01); *H03F 2200/168* (2013.01); *H03F 2200/171* (2013.01); *H03F 2200/408* (2013.01); *H03F 2203/45362* (2013.01); *H03F 2203/45512* (2013.01); *H03F 2203/45528* (2013.01); *H03F 2203/45544* (2013.01); *H03F 2203/45631* (2013.01); *H03F 2203/45686* (2013.01); *H03F 2203/45726* (2013.01)

(56) References Cited

U.S. PATENT DOCUMENTS

| | | | | |
|---|---|---|---|---|
| 6,262,628 | B1* | 7/2001 | Shinomiya | H03F 3/45089 330/252 |
| 6,590,452 | B1 | 7/2003 | van Rhijn | |
| 7,688,140 | B2* | 3/2010 | Yuasa | H03F 3/3022 330/252 |
| 2003/0207679 | A1* | 11/2003 | Kaczynski | H03H 11/0433 455/339 |
| 2004/0008086 | A1 | 1/2004 | Sanchez et al. | |
| 2006/0007221 | A1* | 1/2006 | Eaton | H04N 17/04 345/207 |
| 2006/0119429 | A1* | 6/2006 | Lim | H03F 3/189 330/253 |
| 2006/0189881 | A1 | 8/2006 | Fassio et al. | |
| 2007/0096799 | A1* | 5/2007 | Marais | H03H 11/04 327/557 |
| 2008/0077039 | A1* | 3/2008 | Donnett | A61B 5/0006 600/544 |
| 2008/0290944 | A1* | 11/2008 | Sarpeshkar | H03F 1/0266 330/261 |
| 2008/0294062 | A1 | 11/2008 | Rapoport et al. | |
| 2009/0115516 | A1* | 5/2009 | Park | H03F 3/45183 330/253 |
| 2009/0171236 | A1* | 7/2009 | Davies | A61B 5/0537 600/547 |
| 2010/0036211 | A1* | 2/2010 | La Rue | A61B 5/0002 600/301 |
| 2010/0274114 | A1* | 10/2010 | Denker | A61B 5/04012 600/373 |
| 2011/0061947 | A1* | 3/2011 | Krah | G06F 1/3215 178/18.01 |
| 2011/0092834 | A1* | 4/2011 | Yazicioglu | A61B 5/0402 600/509 |
| 2012/0044021 | A1* | 2/2012 | Yeh | H03F 1/0205 330/257 |
| 2013/0116577 | A1* | 5/2013 | Yazicioglu | A61B 5/04017 600/483 |
| 2013/0169361 | A1* | 7/2013 | Killat | H03F 3/45183 330/253 |
| 2013/0237874 | A1* | 9/2013 | Zoicas | A61B 5/0452 600/521 |
| 2013/0307623 | A1* | 11/2013 | Dusad | H03F 3/45 330/261 |

OTHER PUBLICATIONS

European Patent Office, Extended Supplemental Search Report (ESSR) issued on Oct. 31, 2014 for corresponding European Patent Application No. 12801854.6 (PCT/US2012043173) pp. 1-7 and claims pp. 8-10 (pp. 1-10).

Yi-Kai Lo, Wentai Liu, Kuanfu Chen, Ming-Hsien Tsai, and Fu-Lung Hsueh, "A 64-Channel neuron recording system," IEEE EMBS, Aug. 2011.

Korean Intellectual Property Office, International Search Report issued on Mar. 29, 2013 for corresponding international patent application No. PCT/US2012/043173 (pp. 1-3) with claims searched (4-5) pp. 1-5.

M. A. Nicolelis, J. K. Chapin, Controlling robots with the mind., Scientific American, United States, vol. 287 No. 4, pp. 46-53, 2002.

M. A. L. Nicolelis, "Actions from thoughts." Nature, 2001.

W. Wattanapanitch, M. Fee, and R. Sarpeshkar, "An energy efficient micropower neural recording amplifier." IEEE Trans. Biomed Circuits Sys., vol. 1, No. 2, pp. 136-147, Jun. 2007.

Matthew J. Nelson, Pierre Pouget, Erik A. Nilsen, Craig D. Patten, and Jeffrey D. Schall, "Review of signal distortion through metal microelectrode recording circuits and filters," Journal of Neuroscience Methods, vol. 169, iss. 1, pp. 141- 157, Mar. 30, 2008.

M. Manghisoni, L. Gaioni, L. Ratti, Member, IEEE, V. Re, V. Speziali, and G. Traversi, "Impact of gate-leakage current noise in sub-100 nm CMOS front-end electronics," IEEE Nuclear Science Sym. Conf. Record, vol. 5, pp. 12503-2508, 2007.

Thanachayanont, A. and Naktongkul, P "Low-voltage wideband compact CMOS variable gain amplifier," IEEE Electron. Lett., vol. 41, iss. 2, pp. 51-52, 2005.

J. M. Mollazadeh, K. Murari, G. Cauwenberghs, and N. Thakor, "Micropower CMOS integrated low-noise amplification, filtering, and digitization of multimodal neuropotentials," IEEE Trans. Biomed. Circuits Syst., vol. 3, No. 1, pp. 1-10, Feb. 2009.

B. Gosselin, A. E. Ayoub, J.-F. Roy, M. Sawan, F. Lepore, A. Chaudhuri, and D. Guitton, "A Mixed-Signal Multichip Neural Recording Interface With Bandwidth Reduction," IEEE Trans. on Biomed. Circuits and Systems, vol. 3, No. 3, pp. 129-141, Jun. 2009.

Rikky Muller, Simone Gambini, Jan M. Rabaey, "A 0.013mm2 5μW DC-Coupled Neural Signal Acquisition IC with 0.5V Supply ," ISSCC Dig. Tech. Papers, Feb. 2011.

State Intellectual Property Office of the Peoples Republic of China—2nd Office Action and English translation with claims as examined; app. No. 201280035320.X, issued Oct. 13, 2015, pp. 1-8, counterpart to this U.S. Appl. No. 14/107,118.

State Intellectual Property Office of the Peoples Republic of China—3nd Office Action and English translation with claims as examined; app, No. 201280035320.X, issued Oct. Apr. 5, 2016, pp. 1-11, counterpart to this U.S. Appl. No. 14/107,118.

Japanese Patent Office—1st Office Action and English translation with claims as examined; app No. 2014-517097, issued Mar. 15, 2016, pp. 1-8, counterpart to this U.S. Appl. No. 14/107,118.

\* cited by examiner

NEURAL RECORDING SYSTEM

CROSS-REFERENCE TO RELATED APPLICATIONS

This application is a 35 U.S.C. §111(a) continuation of PCT international application number PCT/US2012/043173 filed on Jun. 19, 2012, incorporated herein by reference in its entirety, which is a nonprovisional of U.S. provisional patent application Ser. No. 61/571,098 filed on Jun. 20, 2011, incorporated herein by reference in its entirety. Priority is claimed to each of the foregoing applications.

The above-referenced PCT international application was published as PCT International Publication No. WO 2012/177654 on Dec. 27, 2012 and republished on Jul. 4, 2013, which publications are incorporated herein by reference in their entireties.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

BACKGROUND OF THE INVENTION

1. Field of the Invention

This invention relates to methods, devices and system for recording of electrical signals from neurons.

2. References

[1] M. A. Nicolelis, J. K. Chapin, Controlling robots with the mind., Scientific American, United States, vol. 287 no. 4, pp. 46-53, 2002.

[2] M. A. L. Nicolelis, "Actions from thoughts." *Nature*, 2001.

[3] W. Wattanapanitch, M. Fee, and R. Sarpeshkar, "An energy efficient micropower neural recording amplifier." *IEEE Trans. Biomed. Circuits Sys.*, vol. 1, no. 2, pp. 136-147, June 2007.

[4] Matthew J. Nelsona, Pierre Pougeta, Erik A. Nilsenc, Craig D. Pattenc, and Jeffrey D. Schalla, "Review of signal distortion through metal microelectrode recording circuits and filters," *Journal of Neuroscience Methods*, vol. 169, iss. 1, pp 141-157, 30 March 2008.

[5] M. Manghisoni, L. Gaioni, L. Ratti, Member, IEEE, V. Re, V. Speziali, and G. Traversi, "Impact of gate-leakage current noise in sub-100 nm CMOS front-end electronics," *IEEE Nuclear Science Sym. Conf. Record*, vol. 5, pp. 12503-2508, 2007.

[6] Thanachayanont, A. Naktongkul, "Low-voltage wideband compact CMOS variable gain amplifier," *IEEE Electron. Lett.*, vol. 41, iss. 2, pp. 51-52, 2005.

[7] David Johns, Ken Martin, Analog Integrated Circuit Design, Wiley, 1997.

[8] J. M. Mollazadeh, K. Murari, G. Cauwenberghs, and N. Thakor, "Micropower CMOS integrated low-noise amplification, filtering, and digitization of multimodal neuropotentials," *IEEE Trans. Biomed. Circuits Syst.*, vol. 3, no. 1, pp. 1-10, February 2009.

[9] B. Gosselin, A. E. Ayoub, J.-F. Roy, M. Sawan, F. Lepore, A. Chaudhuri, and D. Guitton, "A Mixed-Signal Multichip Neural Recording Interface With Bandwidth Reduction," *IEEE Trans. on Biomed. Circuits and Systems*, vol. 3, no. 3, pp. 129-141, June 2009.

[10] Rikky Muller, Simone Gambini, Jan M. Rabaey, "A 0.013 $mm^2$ 5 µW DC-Coupled Neural Signal Acquisition IC with 0.5V Supply," *ISSCC Dig. Tech. Papers, February*, 2011.

[11] Yi-Kai Lo, Wentai Liu, Kuanfu Chen, Ming-Hsien Tsai, and Fu-Lung Hsueh, "A 64-Channel neuron recording system," *IEEE EMBS, August*, 2011.

3. Description of Related Art

Understanding how the brain functions by recording the electrical activity of brain cells (neurons) has been pursued by neuroscientists and clinicians. The underlying mechanism of how neurons fire and interact can be translated into skilled and precise movements, and understanding the mechanism can be used as a tool for diagnosing brain diseases. It has been shown that recorded neuron activities from the motor cortex can be used to control a robotic device [1]-[2]. Neuroscientists have employed neuron recording from scalp or chronically implanted intracranial electrodes to investigate the electrophysiological activity for epileptic seizure detection and prediction [2]. Those experiments involved recording a large population of neurons and thus stimulated the need for the development of a multi-channel neuron recording system.

Challenges of designing a neuron recording system is highly correlated with the characteristics of the physiological neuron signals. The recording device must be able to record these signal with a large dynamic range in terms of signal amplitude and frequency, and to reject the DC offset occurring at the electrode-electrolyte interface. Power consumption of the system has to be reduced for long-term operation and to avoid elevating the temperature of brain tissue which could cause permanent damages [3]. The electrode impedance and amplifier input impedance form a voltage divider and thus the practical neuron signal shown at amplifier input is smaller than its actual value.

The degradation is severe for local field potentials (LFPs) recording because electrode impedance is much higher at 10 Hz than its value at 1-kHz [4]. If the neural signal at the recording amplifier input is seriously attenuated, it is difficult to be differentiated from the background noise. In addition, the next generation of this recording system should have the capability to process an enormous amount of neural information via signal detection, feature extraction, pattern classification and other mechanisms. A future recording system should also have the capability of reducing the amount of data to be transmitted and/or extracting a stable control signal from a large neuron pool in order to control prosthetic devices. The design challenges noted above can be translated into low-voltage and low-power design necessitating an advanced technology node. The present invention addresses at least some of these challenges.

BRIEF SUMMARY OF THE INVENTION

This invention provides a fully integrated low-power neuron recording front-end system in TSMC 65 nm 1p6m MOS technology. The system is expandable to support thousand of channels. In one example, we have two recording modules, each containing 32 recording channels with tunable bandwidth and gain, a 32-to-1 multiplexer, one differential successive approximation register (SAR) analog-to-digital converter (ADC) with programmable sampling rate on each channel, and a digital control module to govern the signal digitization as well as to encode and serialize the digitized neuron signal from two ADCs. Results for both post-layout simulations and real chip measurements are agreeable. The results show the recording amplifier consumes 6 μW with an input-referred noise of 3.8 μVrms. The ADC can digitize the neural signal at a sampling rate of 40 kS/s at 9-bit resolution. The overall power consumption of the entire system is 2.56 mW and occupies an area of 3×4 mm$^2$.

The invention according to an exemplary embodiment includes the following features:

(a) Scalable architecture of analog front-end to support high density of channel for neural recording system, even >1,000 channels.

(b) Fully integrated low power/low noise chip design of analog front end including 3-stage amplifiers and SAR ADC using deep submicron CMOS process technology such as 65 nm, 45 nm, 22 nm, etc CMOS process.

(c) Low power and low noise design by a special gain-boosted folded-cascode amplifier to enhance amplifier's open-loop gain while simultaneously reducing the input-referred noise.

(d) The amplifier has a high input impedance and is capable of supporting programmable gain (47-59 dB) and programmable bandwidth (0.1 Hz-12 KHz), for local field potential and action potential for neural signal processing, as well as other applications such as environmental and chemical agent detections.

(e) Programmable bandwidth is achieved by tuning the bias voltage of series of transistors operating at weak inversion region as well as the loading capacitance.

(f) Each 9-bit SAR ADC with variable sampling rate and is shared by 32 channels of amplifiers via 32:1 multiplexor, thus the data of 32 channels is serialized and output via wired or wireless communication.

In one embodiment, a fully integrated neural amplifier using gain-boosting is provided for local field potentials (LFP), neural spikes, ECoG signals from biological subjects. Two electrodes, working electrode and counter electrode, are connected to the DC block capacitor, $C_{in}$, of the neural amplifier. While a ground/reference electrode connects the body ground to circuit ground of the amplifier. A capacitive feedback configuration sets the gain of the neural amplifier as the ratio of the input capacitor ($C_{in}$) and feedback capacitor ($C_f$). The parasitic effects from $C_{par}$, $C_{in}$, and $C_f$ can be suppressed by the enhanced open-loop gain of the amplifier to minimize gain distortion, where $C_{par}$ is the parasitic capacitance of the input transistors operating in sub-threshold region.

Open-loop gain enhancement of the amplifier is achieved by incorporating an auxiliary amplifier into a conventional folded-cascode (FC) amplifier while still consuming the comparable amount of current to a conventional FC amplifier. The overall gain of the amplifier is the summation of gain of the FC amplifier and the auxiliary amplifier.

The auxiliary amplifier for gain enhancement is achieved by two common-source (CS) amplifiers. The first amplifier can be formed by a differential pair with diode-connected load or a current source load. Outputs of the first amplification stage are connected to the two gates of current source transistors of the FC amplifier, respectively, which are used as the second CS amplifier. The second CS amplifier is embedded into the folded branch of the FC amplifier for the purpose of minimizing current consumption.

The input signal is amplified by two routes (see FIG. 3): one is through the differential input pair of the FC amplifier, $M_{1a-1b}$; the other is amplified by the first CS amplifier of $M_{1c-d}$ and $M5_{a-b}$ as well as the second CS amplifier formed by $M_{4a-b}$ and the impedance seen from $M_{4a}$ drain. The overall gain of the gain-boosted amplifier is derived as $$\text{Gain} = g_{m1} R_{out} + g_{m1}(2\alpha - 1)\frac{g_{m4}}{g_{m5}} R_{out} \qquad (1)$$

$$= g_{m1}\left(1 + \frac{g_{m4}}{g_{m5}}(2\partial - 1)\right)((1 + (g_{m3} r_{03}) r_{05}) // r_{04})$$

where $g_{mi}$ and $r_{oi}$ are the transconductance and output resistance corresponding to transistor $M_i$, and $\alpha$ is the current distribution ratio ($0.5 < \alpha < 1$) The gain of the amplifier is boosted $(1+g_{m4}/g_{m5}(2\alpha-1))$ times as shown in equation 1 by using the gain boosted technique.

Through the gain enhancement technique, a small input capacitor of the neural amplifier can be used to achieve larger input impedance such that signal distortion/attenuation between the electrode and amplifier interface is reduced. 5 pF capacitor is used to result in the input impedance of 31.8 Mohm at 1 kHz.

Smaller $C_{in}$ reduce the silicon area of the amplifier, which enables the implementation of multi-channel recording with less silicon area.

The neural amplifier is integrated monolithically on a single semiconductor chip. No external/off-chip capacitor is required.

The neural amplifier structure is applicable for modern sub-100 nm CMOS technology, in which a low supply voltage, smaller output resistance, and larger leakage current emerge.

The input differential transistor pair of the neural amplifier is implemented with thick oxide I/O devices to prevent significant gate leakage current in modern sub-100 nm CMOS technology.

Low power consumption of 4 μW or less is achieved by biasing the input differential transistor pair of the neural amplifier in sub-threshold region.

Low input-referred noise for the gain-boosted amplifier is achieved by (a) reducing the current flowing in the folded branch of an conventional FC amplifier, i.e. reduce the noise contribution from the cascaded transistors, and (b) increasing open loop-gain of the amplifier with the gain-boosted technique.

The input-referred noise power density of the neural amplifier with gain boost technique and an FC amplifier are shown in equation 2 and equation 3, respectively.

$$\overline{v_{rms,n}^2} = \frac{4KT}{\kappa}\left(\frac{1}{\left(g_{m1} + g_{m1}(2\alpha - 1)\frac{g_{m4}}{g_{m5}}\right)}\right) + \qquad (2)$$

$$\frac{8KT\gamma g_{m2}}{\left(g_{m1} + g_{m1}(2\alpha - 1)\frac{g_{m4}}{g_{m5}}\right)^2} + \frac{16KT\gamma g_{m4}}{\left(g_{m1} + g_{m1}(2\alpha - 1)\frac{g_{m4}}{g_{m5}}\right)^2}$$

and $$\overline{v_{rms,n}^2} = \frac{4KT}{\kappa}\left(\frac{1}{g_{m1}}\right) + \frac{16KTg_{m2}}{3g_{m1}^2} + \frac{16KTg_{m4}}{3g_{m1}^2} \qquad (3)$$

where K is the Boltsmann constant, κ is the sub-threshold gate coupling coefficient, $g_{mi}$ is the transconductance corresponding to transistor $M_i$, T is the absolute temperature, α is the current distribution ratio in the amplifier, γ is the thermal noise coefficient, and α is the current distribution ratio ($0.5 < \alpha < 1$). The term $g_{mi}(2\alpha-1)g_{m4}/g_{m5}$ in the denominator stems from the boosted gain of the amplifier to lowers the noise power density. Note that $g_{m4}$ in equation 2 is also smaller than in equation 3 due to the reduced current in the folded branch of the amplifier. Thus, from equations 2 and 3 the input-referred noise of the neural amplifier is suppressed by the gain-boost technique with a moderate choice of α.

The neural amplifier can be disabled once it is malfunctioned after implantation to prevent damage to the subjects.

BRIEF DESCRIPTION OF THE SEVERAL VIEWS OF THE DRAWING(S)

DETAILED DESCRIPTION OF THE INVENTION

Figure 1:
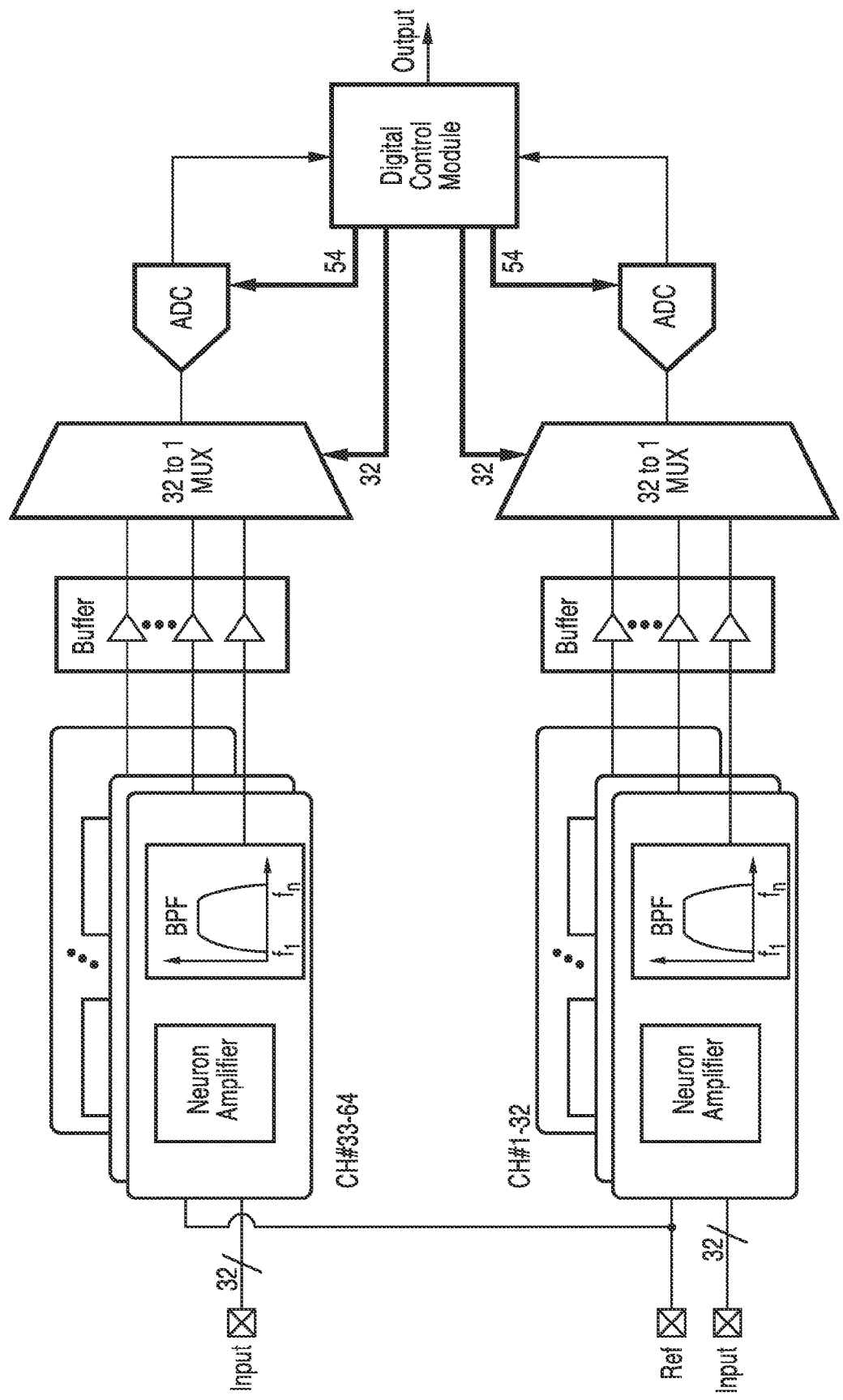
FIG. 1 shows an architecture of a 64-channel recording system according an exemplary embodiment of the present invention.

The overall system architecture is shown in FIG. 1. An exemplary embodiment of the 64-channel system includes two 32-channel recording units and a shared digital controller module (DCM). Each recording unit contains 32 recording channels, one 32-to-1 multiplexer, and an SAR ADC. Within each channel, the neuron amplifier first magnifies the infinitesimal neuron signal. A programmable gain and bandwidth filter is cascaded and configured based on the signal of interests. Buffer at each channel passes the filtered output to the multiplexer. The ADC then digitizes the signal with a sampling rate of 40 kS/s per channel and feeds the output to DCM for data serialization and performing channel-specific processing to identify multi-site components.

Circuit Design

Single Recording Channel

Figure 2:
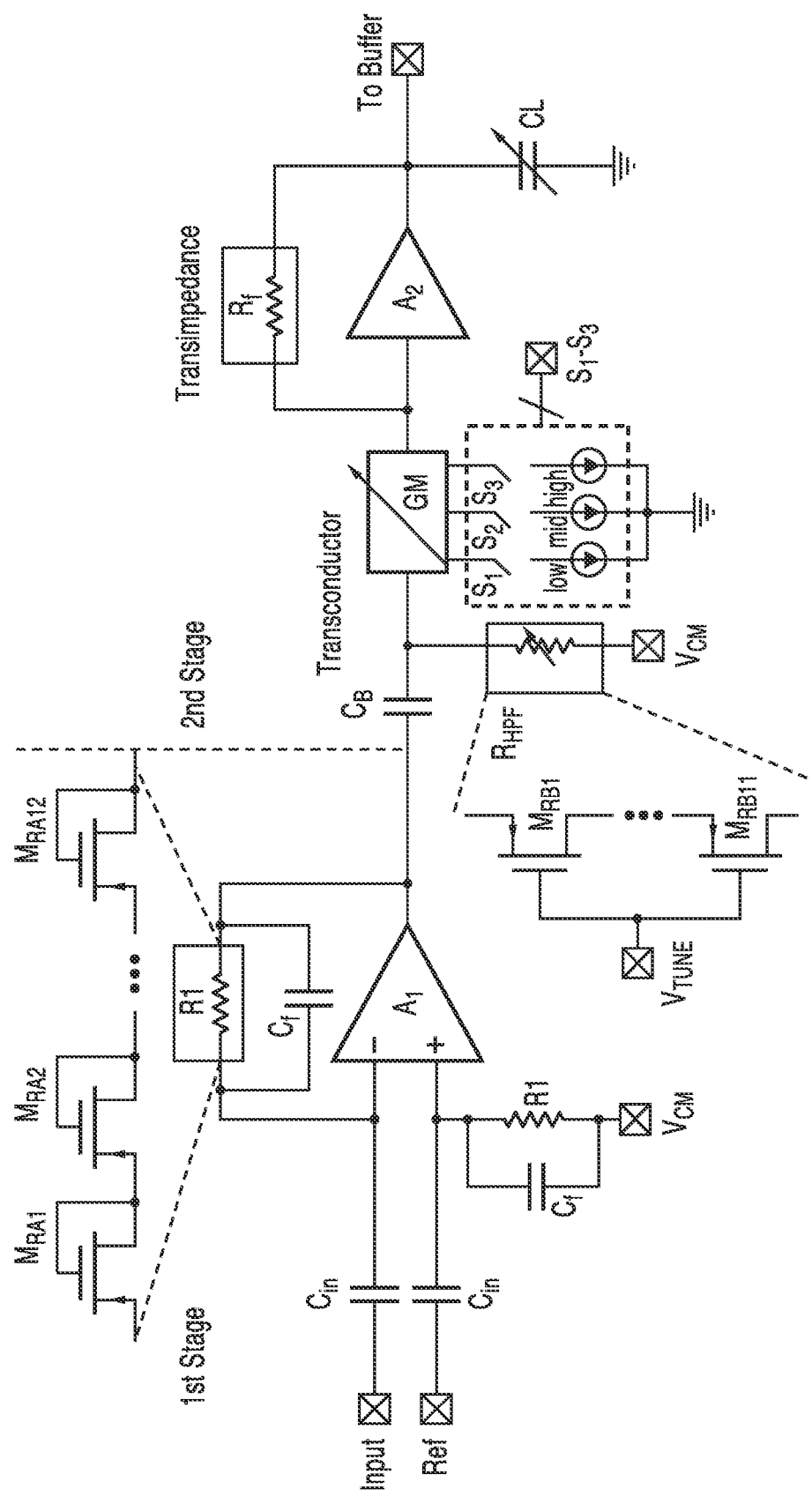
FIG. 2 shows a schematic of one neuron recording channel according an exemplary embodiment of the present invention.

A schematic of one neuron recording channel is shown in FIG. 2. The first stage adopted an AC-coupled amplifier and provided a mid-band amplification of 39.6 dB. The high-pass cutoff frequency of this amplifier is set by the MOS-bipolar pseudo-resistor formed by $M_{RA1-RA12}$ and the feedback capacitor, $C_f$. The high-pass and low-pass cutoff frequencies of the subsequent bandpass filter can be adjusted by tuning $V_{tune}$ to change $R_{HPF}$ and by altering the value of $C_L$, where $R_{HPF}$ is formed by PMOS transistors $M_{RB1-RB11}$ operating in weak inversion and $C_L$ is the load capacitor of the bandpass filter. The recording channel has the capability to adjust its gain from 47 dB to 59 dB. A critical issue rising from using a sub-100 nm process is the increased gate-leakage current compared to the less advanced process. A difference of 2 Å in the gate oxide thickness can lead to an order of magnitude change in the gate-leakage current [5]. Therefore, in our design $M_{RA1-RA12}$, $M_{RB1-RB12}$, and input transistors of amplifier $A_1$ are implemented with thick-oxide I/O transistors to reduce the leakage current, which increases the amplifier noise and lower the resistance of the pseudo-resistor.

Gain-Boosted Amplifier

The mid-band gain of the neuron amplifier can be approximated as $$\frac{V_{out}}{V_{in}} \approx \frac{C_{in}}{\frac{C_{in}+C_f+C_{par}}{A_1}+C_f} \quad (4)$$

where $C_{par}$ and $A_1$ are the parasitic capacitance of the input transistors and the open-loop gain of the amplifier, respectively. Input capacitance ($C_{in}$) is expected to be small, i.e. in the range of several pF, to achieve high input impedance of tens of Mega ohms, while feedback capacitance ($C_f$) must also be reduced to achieve a reasonable gain, for example 40 dB. Though gain error is acceptable for neuron amplifier, a high open-loop gain is still desired to suppress the parasitic effect resulting from large size input transistor and capacitors. However, a high gain is difficult to achieve under the constraint of low supply voltage of 1.2V and power limitation.

Figure 3:
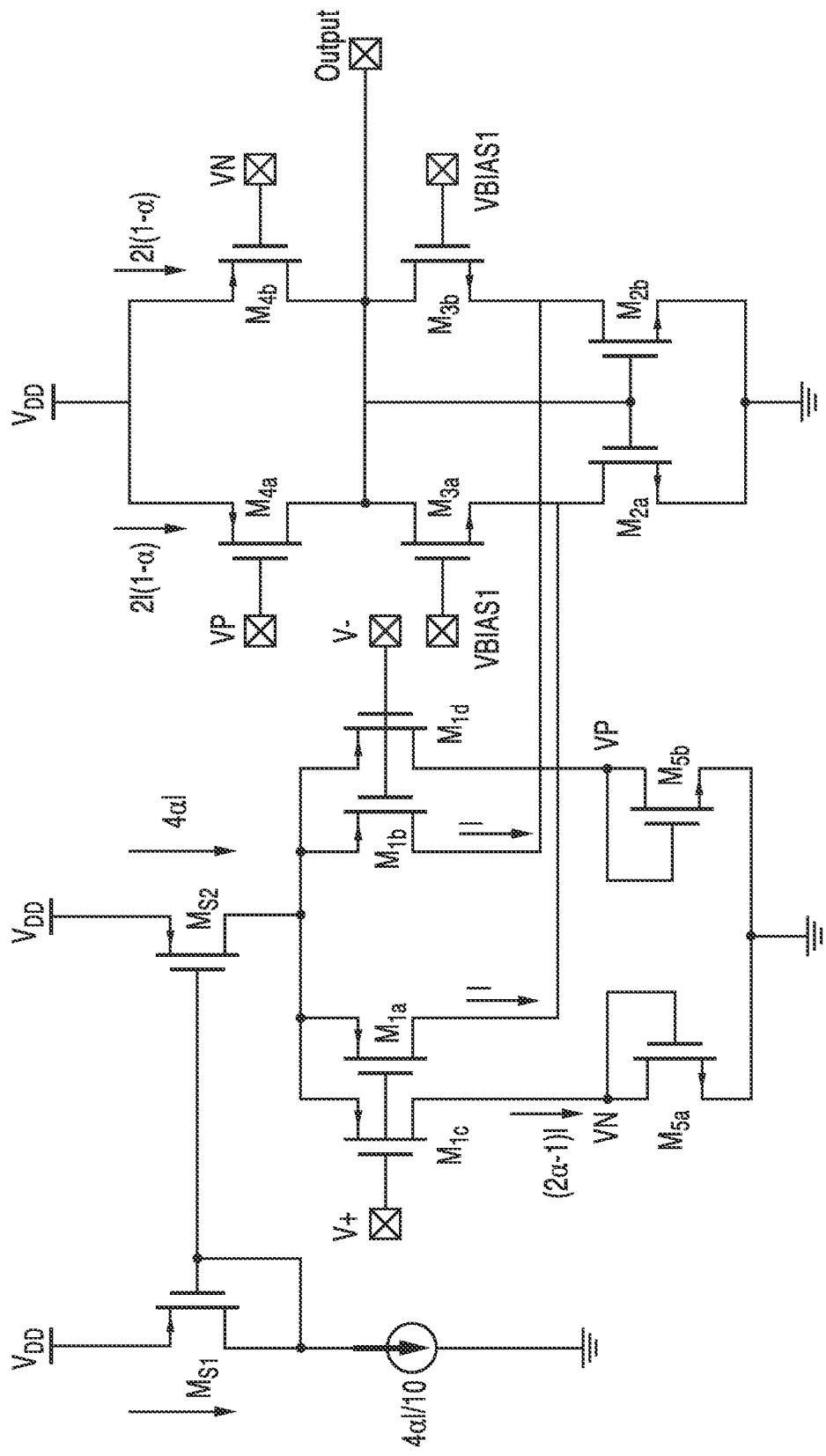
FIG. 3 shows a schematic of the gain-boosted amplifier according an exemplary embodiment of the present invention.

As shown in FIG. 3, we designed a gain-boosted folded-cascode amplifier to enhance amplifier's open-loop gain while simultaneously reducing the input-referred noise. For the biasing condition of the amplifier only a small fraction of overall current is flowing into the folded branch of $M_3$-$M_4$ reducing its noise contribution. Nonetheless under 1.2V supply voltage, it is impractical in our design to add a source degenerated resistor to lower the noise from $M_2$. We utilized the fraction of current taken from $M_2$ to build an auxiliary gain stage formed by $M_{1c-d}$ and $M_{5a-b}$. The additional gain stage enhanced the gain of the amplifier to $1+(2\alpha-1)g_{m4}/g_{m5})$ times and simultaneously reduced the noise from $M_2$. By biasing the input differential transistor $M_1$ into sub-threshold region, the input-referred noise of the amplifier can be derived as equation 2 (see summary). Equation 2 demonstrates the input-referred noise can be reduced by using the gain-boosted topology. Note that $g_{m2}$ and $g_{m4}$ in equation 2 are small due to the reduced current flowing through. The value of $C_{in}$ and $C_f$ is chosen as 5 pF and 50 fF for input impedance, noise, and power tradeoff.

Variable Gain Bandpass Filter (BPF)

The variable gain BPF aims to provide independent tuning capabilities of gain and bandwidth in one single stage to reduce the power consumption. This filter is composed of a cascade of a transconductor and a transimpedance amplifier with a load capacitor, and an RC first order high pass filter as shown in FIG. 2. The voltage gain of the filter is decided by the product of transductance GM and $R_f$, which is the feedback resistor of the transimpedance amplifier. Thus, the gain can be adjusted by setting the current flowing in the transconductor. The variable gain bandpass can provide 7 dB-19 dB gain within a given bandwidth.

Neuron Signal Digitization

A differential charge-redistribution SAR ADC is designed to digitize 64-channel neuron signals. The ADC architecture has unit capacitance of 20 fF. An ADC controller and a multiplexer controller are incorporated in the DCM. A 32:1 multiplexer is placed in front of each ADC to select the channel for sampling. Although using a 5-bit counter to sequentially loop from channel 1 to 32 is straightforward, it may not be the most desirable method in all circumstances. For example, not all of the channels have proper input to be sampled at any time, and the user might only be interested in a subset of channels. Therefore, a channel-of-interest feature is implemented in the multiplexer controller. This enables the user to choose an arbitrary subset of channels, and turn off the rest in order to save power. Some of the channels can even have a higher sampling frequency than others.

Figure 4:
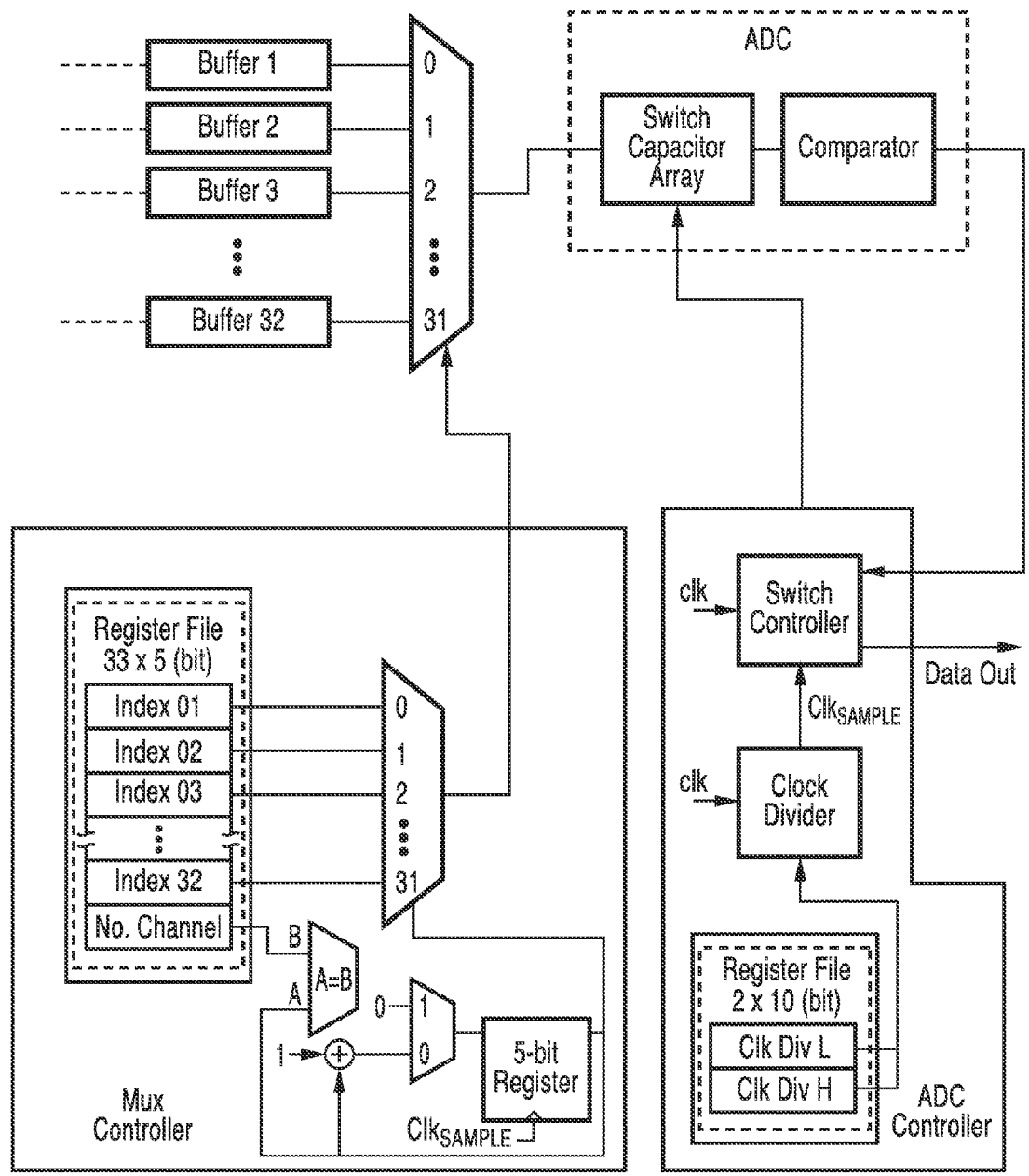
FIG. 4 shows a schematic of analog-to-digital converter (ADC) and digital controller module (DCM) according an exemplary embodiment of the present invention.

FIG. 4 shows an example of the architecture of this multiplexer controller. A 33×5 register file is employed to store the sampling channel indices as well as the number of channels that will be used. To enable a subset of four specific channels, say ch1, ch10, ch19, and ch28, the register file should be filled with 1, 10, 19, and 28 in the first four entries, and 3 in the last entry. The 5-bit counter will loop from 0-3, thus the desired channel indices will be sent to the channel multiplexer sequentially to enable these channels, and all other channels will not be sampled. If the third entry in the previous example is replaced by ch1, then ch1 will be sampled when the 5-bit counter is either 0 or 2, so it has twice the sampling frequency of ch10 and ch28. Thus, a channel can be filled into multiple entries in the register file to achieve a sampling frequency up to 16 times higher than others.

A programmable 20-bit clock divider is implemented in the ADC controller and serves two purposes: to dissociate the sampling frequency and the oscillator frequency; to provide a flexible sampling frequency setting for each ADC. There are two ADCs in this system, so a high frequency oscillator is required for data stream handling. The clock divider can generate appropriate clock frequency for ADC operation no matter what frequency the oscillator is. In addition, since the channel-of-interest feature allows the user to enable a subset of channels, the accumulated frequency is lower in this mode. Thus, the clock divider can be used to set the accumulated sample frequency for each individual ADC based on the number of activated channels and the desired sample frequency per channel.

Simulation Results

Figure 5:
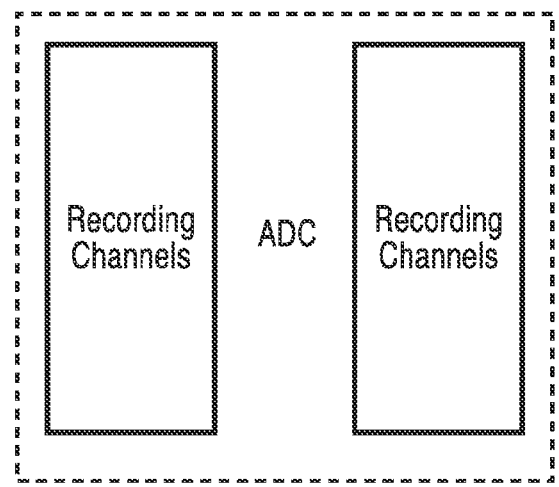
FIG. 5 shows a layout of a 64-channel recording system according an exemplary embodiment of the present invention.

An exemplary 64-channel neuron recording system was designed and under fabrication in TSMC 65 nm CMOS process. The entire system is operated and simulated under 1.2V supply while consuming 40 µW per channel. Note that only 6 µW is consumed by the neuron recording amplifier and BPF. The chip layout occupies an area of 3×4 mm², as shown in FIG. 5. The exemplary layout and power consumption are not optimized for testing purpose.

Figure 6:
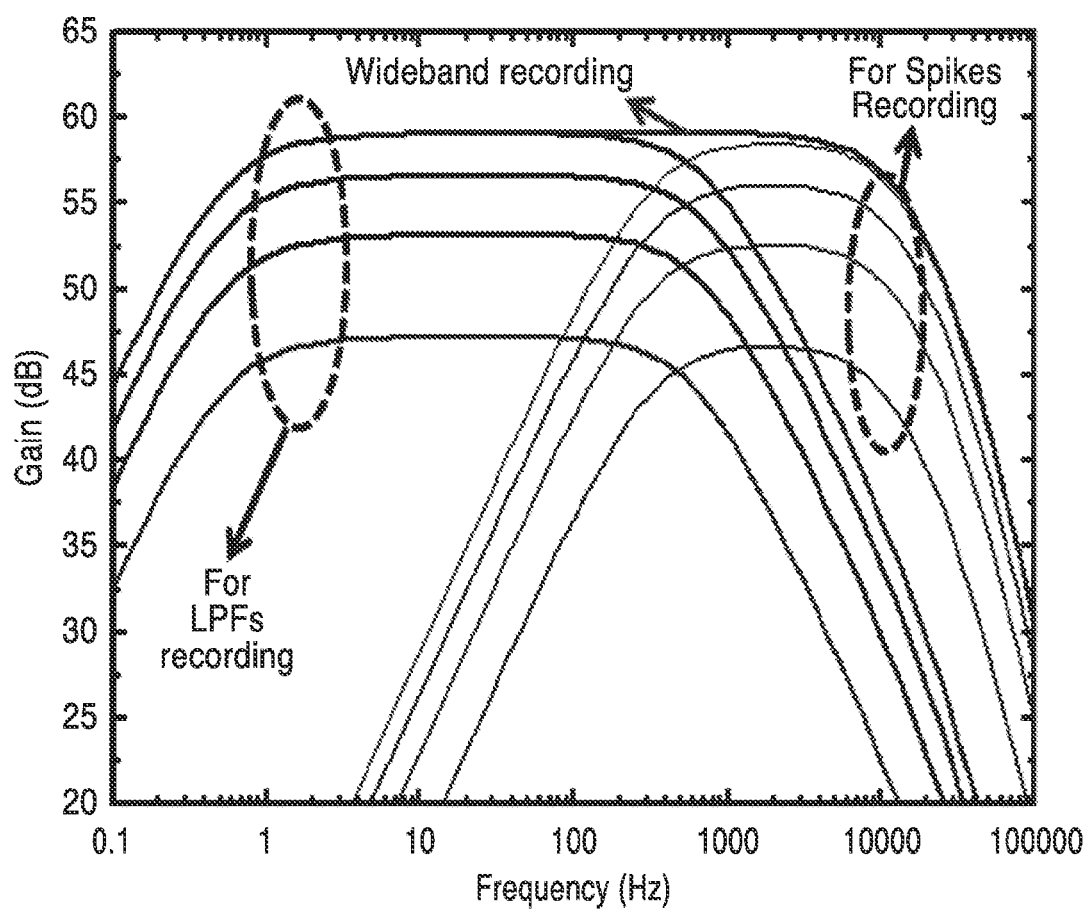
FIG. 6 shows a frequency response of one recording channel according an exemplary embodiment of the present invention.

FIG. 6 shows the frequency responses of one neuron recording channel. For recording LFPs, the system exhibits a programmable gain from 47 dB to 59 dB within the bandwidth from 0.5 Hz to 500 Hz. While with the immediate setting for spike recording, the system provides variable gain from 46.5 dB to 58.5 dB from 300 Hz 12 kHz.

Figure 7:
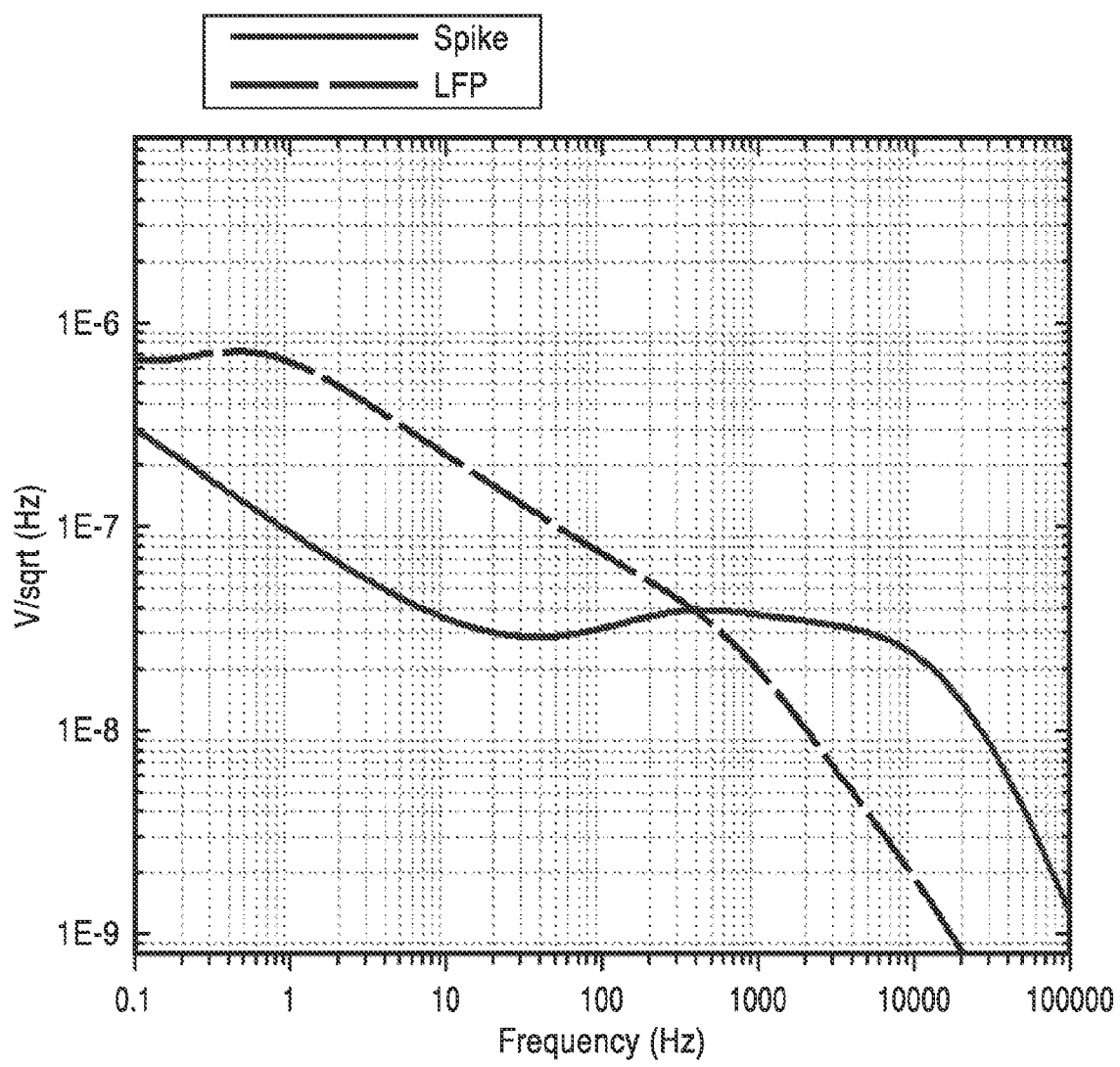
FIG. 7 shows a simulated input-referred noise of the neuron recording channel for local field potentials (LFPs) and spikes recording setting according an exemplary embodiment of the present invention.

Note that the gain of spike recording is slightly lower than that of LFPs because of smaller $R_{HPF}$ value, which lowers the overall output impedance of neuron amplifier. The simulated input-referred noise for both configurations of LFPs and spikes recording is shown in FIG. 7. For LFPs recording, 1/f noise still dominates and thus it is difficult to distinguish the thermal noise level. The overall input-referred noise for both recording settings are 2 $\mu V_{rms}$ (integrating from 0.1 Hz to 5 kHz) and 3.8 $\mu V_{rms}$ (integrating from 30 Hz to 100 kHz) under 47 dB gain configuration. Note that the noise integrating bandwidth here is much larger than the signal bandwidth. Since the popular NEF metric [3] only concerns the current of the amplifier, it cannot reflect the power efficiency. Thus we compared both NEF and the modified metric [10]

$$NEF^2 * VDD = \overline{v_{rms,in}^2}\left(\frac{2P}{\pi * kT/q * 4kT * BW}\right) \quad (5)$$

where P is the power consumption of the amplifier and BW is the signal bandwidth.

The performance of the neuron recording system and comparison with other works is summarized in Table 1. The recording system has high input impedance of 31.8 Mohm at 1 kHz to mitigate the inevitable signal attenuation at the electrode-amplifier interface. The recording amplifier with bandpass filter presents the lowest $NEF^2*VDD$ product. An ADC with a flexible sampling rate for individual channels further gives the user more flexibility to monitor the neuron signal of interests. The overall power consumption of the entire system is 2.56 mW at a system clock rate of 23 MHz.

TABLE I

PERFORMANCE SUMMARY AND COMPARISON

| Reference | [3] | [8] | [9] | This Work |
|---|---|---|---|---|
| Technology | 0.5 µm CMOS | 0.5 µm CMOS | 0.18 µm CMOS | 65 nm CMOS |
| No. of channels | 1 | 16 | 16 | 64 |
| Supply voltage (V) | 2.8 | 3.3 | 1.8 | 1.2 |
| Mid-band gain (dB) | 40.9 | 39.6 | 70 | 47~59 |
| High-cutoff freq.(Hz) | 0.392~295 | 0.2~94 | 100 | 0.5~0.3k |
| Low-cutoff freq. (Hz) | 45~5.32k | 140~8.2k | 9 . . . 2k | 500, 12k |
| Input referred noise ($\mu V_{rms}$) | 3.06 | 1.94 | 5.4 | 3.8*1, 2.0*2 |
| Input impedance @ 1 kHz (Mohm) | 11.38 | 7.9 | — | 31.8 |
| Power consumption of amplifier (µW) | 7.56 | 26.4 | 8.6 | 6 |
| NEF | 2.37 | 2.9 | 4.9 | 3³ |
| NEF²*VDD | 15.7 | 27.7 | 43.2 | 10.8 |
| ADC sampling rate/per channel | — | 16k or 500 | 30k | 4k~40k |
| Resolution (bits) | — | 7~12 | 8 | 9 |
| Overall power consumption (mW) | — | 1.8 | 0.68 | 2.56 |

[1]with noise integrating bandwidth of 30 Hz to 100 kHz
[2]with noise integrating bandwidth of 0.5 Hz to 5 kHz
[3]for spike recording

What is claimed is:
1. A fully integrated neural amplifier of neural signals, comprising:

(a) a first stage amplifier within a neural amplifier, said first stage amplifier configured for connection to a working electrode and a counter electrode, each said electrode connected to a direct current (DC) blocking capacitor (Cin) as input capacitor;

(b) a capacitive feedback circuit within said first stage amplifier configured for setting a gain of said neural amplifier as a ratio of said input capacitor (Cin) and a feedback capacitor (Cf); and (c) a folded-cascode (FC) amplifier having an auxiliary gain stage incorporated in said first stage amplifier to increase open loop gain by using a gain booster;

(d) wherein said gain booster comprises a first common-source (CS) amplifier, and a second common-source (CS) amplifier;

(e) wherein said first common-source (CS) amplifier is formed by a differential pair of transistors with diode-connected load, and provides said auxiliary gain stage with additional transistors so that a first differential input is coupled to input gates of a first pair of common drain coupled transistors $M_{1c}$, $M_{1a}$, with a second differential input coupled to input gates of a second pair of common drain coupled transistors $M_{1b}$, $M_{1d}$, source connections from transistors $M_{1c}$, $M_{1d}$, are coupled to gates of following transistors in that same stage, while source connections from transistors $M_{1a}$, $M_{1b}$ are output to the folded cascode stage in said second common-source (CS) amplifier in order to increase gain and reduce noise;

(f) wherein the differential outputs of said first common-source (CS) amplifier are connected to gates of separate PMOS current source transistors $M_{4a}$, $M_{4b}$ within said folded-cascode (FC) amplifier, which are used as the second common-source (CS) amplifier;

(g) wherein said second common-source (CS) amplifier is embedded into a folded branch of said folded-cascode (FC) amplifier in order to minimize current consumption;

(h) wherein said differential pair of transistors of said first common-source (CS) amplifier shares a same source with a differential pair of transistors of said auxiliary gain stage, but said auxiliary gain stage drains current with a different ratio than in said first common-source (CS) amplifier; and (i) wherein outputs from said auxiliary gain stage are coupled to said second common source amplifier at a complementary input stage providing it with increased pate-source voltage which increases transconductance.

2. The neural amplifier as set forth in claim 1, wherein said neural amplifier is configured for receiving neural signals as local field potentials (LFP), neural spikes, or ECoG signals.

3. The neural amplifier as set forth in claim 1, wherein said neural amplifier is integrated monolithically on a single semiconductor chip.

4. The neural amplifier as set forth in claim 1, wherein said neural amplifier does not require an external/off-chip capacitor.

5. The neural amplifier as set forth in claim 1, wherein in response to biasing input differential transistors $M_{1a}$, $M_{1b}$, $M_{1c}$, $M_{1d}$ into their sub-threshold region, input-referred noise is reduced using this gain-boosting topology.

6. The neural amplifier as set forth in claim 1, wherein an input signal to said first common-source (CS) amplifier is amplified by a first current path through the differential input pair transistors $M_{1a}$, $M_{1b}$ of the FC amplifier, and by a second current path amplified by the first common-source (CS) amplifier using transistors $M_{1c}$, $M_{1d}$ and $M_{5a}$, $M_{5b}$ as well as the second common-source (CS) amplifier formed by $M_{4a}$, $M_{4b}$ and the impedance seen from transistors $M_{4a}$ drain.

7. The neural amplifier as set forth in claim 1:

further comprising a variable gain bandpass filter coupled to an output of the first stage amplifier;

wherein the variable gain bandpass filter comprises a cascade of a transconductor and a transimpedance amplifier with a load capacitor, and an RC first order high pass filter having a voltage gain determined by a product of the transductance of the transconductor and the feedback resistor of the transimpedance amplifier, whereby the variable gain can be adjusted by setting current flow in the transconductor.

8. A fully integrated neural amplifier for amplifying neural signals, comprising:

(a) a first stage amplifier within a neural amplifier, said first stage amplifier configured for connection to a working electrode and a counter electrode, each said electrode connected to said first stage amplifier through a separate DC blocking capacitor (Cin), as input capacitor;

(b) a capacitive feedback circuit within said first stage amplifier configured for setting a gain of said neural amplifier as a ratio of said input capacitor (Cin) and a feedback capacitor (Cf); and (c) a folded-cascode (FC) amplifier having an auxiliary gain stage incorporated in said first stage amplifier to increase open loop gain by using a gain booster comprising two common-source (CS) amplifiers, in which a first common-source (CS) amplifier is formed by a differential pair of transistors with diode-connected load, so that the differential outputs of said first common-source (CS) amplifier are connected to two gates of current source transistors which comprise a second common-source (CS) amplifier that is embedded into the folded branch of said folded-cascode (FC) amplifier for the purpose of minimizing current consumption;

(d) wherein said auxiliary gain stage utilizes additional transistors so that a first differential input is coupled to input gates of a first pair of common drain coupled transistors $M_{1c}$, $M_{1a}$, with a second differential input coupled to input sates of a second pair of common drain coupled transistors $M_{1b}$, $M_{1d}$, with source connections from transistors $M_{1c}$, $M_{1d}$, coupled to following transistors in that same stage, while source connections from transistors $M_{1a}$, $M_{1b}$ are output to said folded cascode amplifier in order to increase gain and reduce noise;

(e) wherein the differential outputs of said first common-source (CS) amplifier are connected to gates of separate PMOS current source transistors $M_{4a}$, $M_{4b}$ within said folded-cascode (FC) amplifier, which are used as the second common-source (CS) amplifier;

(f) wherein said second common-source (CS) amplifier is embedded into a folded branch of said folded-cascode (FC) amplifier in order to minimize current consumption;

(g) wherein said differential pair of transistors of said first common-source (CS) amplifier shares a same source with a differential pair of transistors of said auxiliary gain stage, but said auxiliary gain stage drains current with a different ratio than in said first common-source (CS) amplifier;

(h) wherein outputs from said auxiliary gain stage are coupled to said second common source amplifier at a complementary input stage providing it with increased gate-source voltage which increases transconductance; and (i) a variable gain bandpass filter coupled to an output of said first stage amplifier, in which the variable gain bandpass filter comprises a cascade of a transconductor and a transimpedance amplifier with a load capacitor, and an RC first order high pass filter having a voltage gain determined by a product of transductance of the transconductor and the feedback resistor of the transimpedance amplifier, thus allowing variable gain to be adjusted by setting current flow in the transconductor.

9. The neural amplifier as recited in claim 8, wherein an input signal to said first common-source (CS) amplifier is amplified by a first current path through the differential input pair of FC amplifier transistors $M_{1a}$, $M_{1b}$, and by a second current path amplified by the first common-source (CS) amplifier using transistors $M_{1c}$, $M_{1d}$ and $M_{5a}$, $M_{5c}$ as well as the second common-source (CS) amplifier formed by $M_{4a}$, $M_{4b}$, and the impedance seen from transistor $M_{4a}$ drain.

10. The neural amplifier as recited in claim 8, wherein said neural amplifier is configured for receiving neural signals are local field potentials (LFP), neural spikes, or ECoG signals.

11. The neural amplifier as recited in claim 8, wherein said neural amplifier is integrated monolithically on a single semiconductor chip.

12. The neural amplifier as recited in claim 8, wherein said neural amplifier does not require an external or off-chip capacitor.

13. The neural amplifier as recited in claim 8, further comprising a pseudo-resistor (R1) in parallel with said feedback capacitor (Cf) to establish a high-pass cutoff frequency of said first stage amplifier.

14. The neural amplifier as recited in claim 8, wherein said neural amplifier is configured for use with a differential charge-redistribution successive approximation register (SAR) analog-to-digital converter (ADC) for digitizing a plurality of neuron signals.

15. The neural amplifier as recited in claim 8, wherein output from the neural amplifier is configured for coupling to a specific input of a multiplexer that is configured to receive inputs from a plurality of said neural amplifiers, with the output of the multiplexer configured for connection to the input of an analog-to-digital converter (ADC) to digitize the analog signals received from a plurality of said neural amplifiers.

* * * * *